US009820909B2

(12) United States Patent
Enlow

(10) Patent No.: US 9,820,909 B2
(45) Date of Patent: Nov. 21, 2017

(54) APPARATUS, SYSTEM, AND METHOD FOR CONCENTRATING A STREAM OF WATER

(76) Inventor: Don L. Enlow, Farmington, UT (US)

( * ) Notice: Subject to any disclaimer, the term of this patent is extended or adjusted under 35 U.S.C. 154(b) by 348 days.

(21) Appl. No.: 13/589,710

(22) Filed: Aug. 20, 2012

(65) Prior Publication Data

US 2013/0046136 A1 Feb. 21, 2013

Related U.S. Application Data

(60) Provisional application No. 61/525,005, filed on Aug. 18, 2011.

(51) Int. Cl.

| | |
|---|---|
| ***A61F 5/00*** | (2006.01) |
| ***A61H 9/00*** | (2006.01) |
| ***A61H 33/00*** | (2006.01) |
| *A61H 19/00* | (2006.01) |

(52) U.S. Cl.

CPC ......... *A61H 9/0021* (2013.01); *A61H 9/0007* (2013.01); *A61H 33/6036* (2013.01); *A61H 19/30* (2013.01)

(58) Field of Classification Search

CPC ...... A61H 9/00; A61H 9/0007; A61H 9/0021; A61H 33/6036

USPC .................................. 600/38–41; 4/448, 596

See application file for complete search history.

(56) References Cited

U.S. PATENT DOCUMENTS

| | | | | |
|---|---|---|---|---|
| 785,824 | A | 3/1905 | Nicholls | |
| 2,383,235 | A | 11/1943 | Brown | |
| 4,123,808 | A | 11/1978 | Guarrera | |
| 5,241,714 | A | 9/1993 | Barry | |
| 5,503,742 | A * | 4/1996 | Farley | 210/238 |
| 5,549,822 | A * | 8/1996 | Ferguson | 210/238 |
| 5,920,923 | A | 7/1999 | Jillette | |
| 5,987,682 | A | 11/1999 | Rossi | |
| 6,145,670 | A * | 11/2000 | Risser | 210/449 |
| 6,315,220 | B1 | 11/2001 | Grubb | |
| 6,395,172 | B1 * | 5/2002 | Koike | 210/282 |
| 6,601,782 | B1 * | 8/2003 | Sandholm et al. | 239/427 |
| 6,641,548 | B2 | 11/2003 | Elnar | |
| 6,770,060 | B2 | 8/2004 | Hoenig | |
| 6,785,915 | B1 * | 9/2004 | Daugherty | 4/448 |
| 6,805,679 | B2 | 10/2004 | Winkley | |
| 8,657,146 | B2 * | 2/2014 | Schultheis et al. | 220/586 |
| 2004/0064074 | A1 | 4/2004 | Kennedy et al. | |
| 2004/0176710 | A1 | 9/2004 | Kennedy et al. | |
| 2006/0041210 | A1 | 2/2006 | Regey | |
| 2006/0111608 | A1 | 5/2006 | Kennedy | |

(Continued)

*Primary Examiner* — John Lacyk
(74) *Attorney, Agent, or Firm* — Kunzler, PC

(57) ABSTRACT

An apparatus, system and method are disclosed for manipulating a user's erogenous zone. The apparatus includes a chamber, a plurality of baffling elements, and a concentration member. The chamber has a first end opposing a second end. The first end of the chamber is communicable in water receiving communication with a water source. The plurality of baffling elements are positioned within the chamber and are configured to interrupt a flow of water received from the first end of the chamber. The concentration member defines a channel having a water receiving end and a water dispensing end. The channel has a converging cross-sectional area in a direction from the water receiving end to the water dispensing end with the water receiving end communicable in water receiving communication with water flowing past the baffling elements.

18 Claims, 9 Drawing Sheets

(56) References Cited

U.S. PATENT DOCUMENTS

| | | | |
|---|---|---|---|
| 2007/0213676 | A1 | 9/2007 | Popoalii |
| 2008/0078408 | A1 | 4/2008 | Park |
| 2010/0010399 | A1 | 1/2010 | Siebert, Jr. |

* cited by examiner

APPARATUS, SYSTEM, AND METHOD FOR CONCENTRATING A STREAM OF WATER

CROSS-REFERENCES TO RELATED APPLICATIONS

This application claims the benefit of U.S. Provisional Patent Application No. 61/525,005 entitled "APPARATUS, SYSTEM, AND METHOD FOR CONCENTRATING A STREAM OF WATER" and filed on Aug. 18, 2011 for Don L. Enlow, which is incorporated herein by reference.

FIELD

This subject matter relates to physical therapy and self-massage and more particularly relates to hydrotherapeutic manipulation of an erogenous zone on a user.

BACKGROUND

Masturbation is the sexual stimulation of an individual's genitals, usually to the point of orgasm. Various medical and psychological benefits have been attributed to a healthy attitude to sex in general and to masturbation in particular. Many mental health professionals believe that masturbation can relieve depression and lead to a higher sense of self-esteem. Masturbation can also be particularly useful in relationships where one partner wants more sex than the other—in which case masturbation provides a balancing effect and thus a more harmonious relationship.

Masturbation can be performed manually, by use of objects or tools, or by some combination of these methods. When performed manually, the individual does not risk the embarrassment associated with another individual finding the object or tool used to masturbate. However, some individuals find manual stimulation lacking in complete satisfaction. Accordingly, these individuals may wish to use an object or tool to stimulate themselves despite the potential for embarrassment if another individual discovers the object or tool used.

SUMMARY

From the foregoing discussion, it should be apparent that a need exists for an apparatus, system, and method for manipulating a user's erogenous zone. Beneficially, such an apparatus, system, and method would provide a discrete and pleasurable experience to the user.

The present invention has been developed in response to the present state of the art, and in particular, in response to the problems and needs in the art that have not yet been fully solved by currently available massaging devices. Accordingly, the present invention has been developed to provide an apparatus, system, and method for manipulating a user's erogenous zone that overcome many or all of the above-discussed shortcomings in the art.

The apparatus to manipulate a user's erogenous zone, in certain embodiments, includes a chamber, a plurality of baffling elements, and a concentration member. The chamber has a first end opposing a second end. The first end of the chamber is communicable in water receiving communication with a water source. The plurality of baffling elements are positioned within the chamber and are configured to interrupt a flow of water received from the first end of the chamber. The concentration member defines a channel having a water receiving end and a water dispensing end. The channel has a converging cross-sectional area in a direction from the water receiving end to the water dispensing end with the water receiving end communicable in water receiving communication with water flowing past the baffling elements.

In one embodiment, the apparatus also includes a coupling member attached to the first end of the chamber with the coupling member removably coupleable with a shower outlet. In certain embodiments, the coupling member is removably coupleable with a conventional shower head. In other embodiments, the coupling member is removably coupleable with a household water source (i.e., a shower pipe).

In an exemplary embodiment, the plurality of baffling elements are a plurality of beads. In such an embodiment, each bead in the plurality of beads may be substantially spherical. In one embodiment, a diameter of an outermost surface of each bead in the plurality of beads is between about 3/16 and 1/2 of an inch. In other embodiments, at least one of a size, a shape, and a number of the baffling elements is selected to impart a vibratory effect to the flow of water flowing past the baffling elements.

In certain embodiments the apparatus includes an elongated fiber and the plurality of baffling elements are coupled to the elongated fiber. In such an embodiment, the elongated fiber retains the plurality of baffling elements in a unified conglomerated of baffling elements.

In another embodiment, the apparatus includes a filtering member positioned between the plurality of baffling members and the concentration member. In such an embodiment the filtering member has at least one aperture. A size of the at least one aperture is substantially smaller than a size of each of the plurality of baffling members to retain the baffling members within the chamber.

In certain embodiments, an inner diameter of the water receiving end of the concentration member is between about 3/4 and 1 1/4 of an inch and wherein an inner diameter of the water dispensing end is between about 1/16 and 7/16 of an inch. Thus, in certain embodiments the concentration member is tapered from the water receiving end to the water dispensing end to concentrate water flowing through the apparatus and increase the water pressure. In another embodiment, the apparatus includes a water velocity adjustment member that allows a user to adjust a velocity of the water dispensed from the dispensing end of the concentration member.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
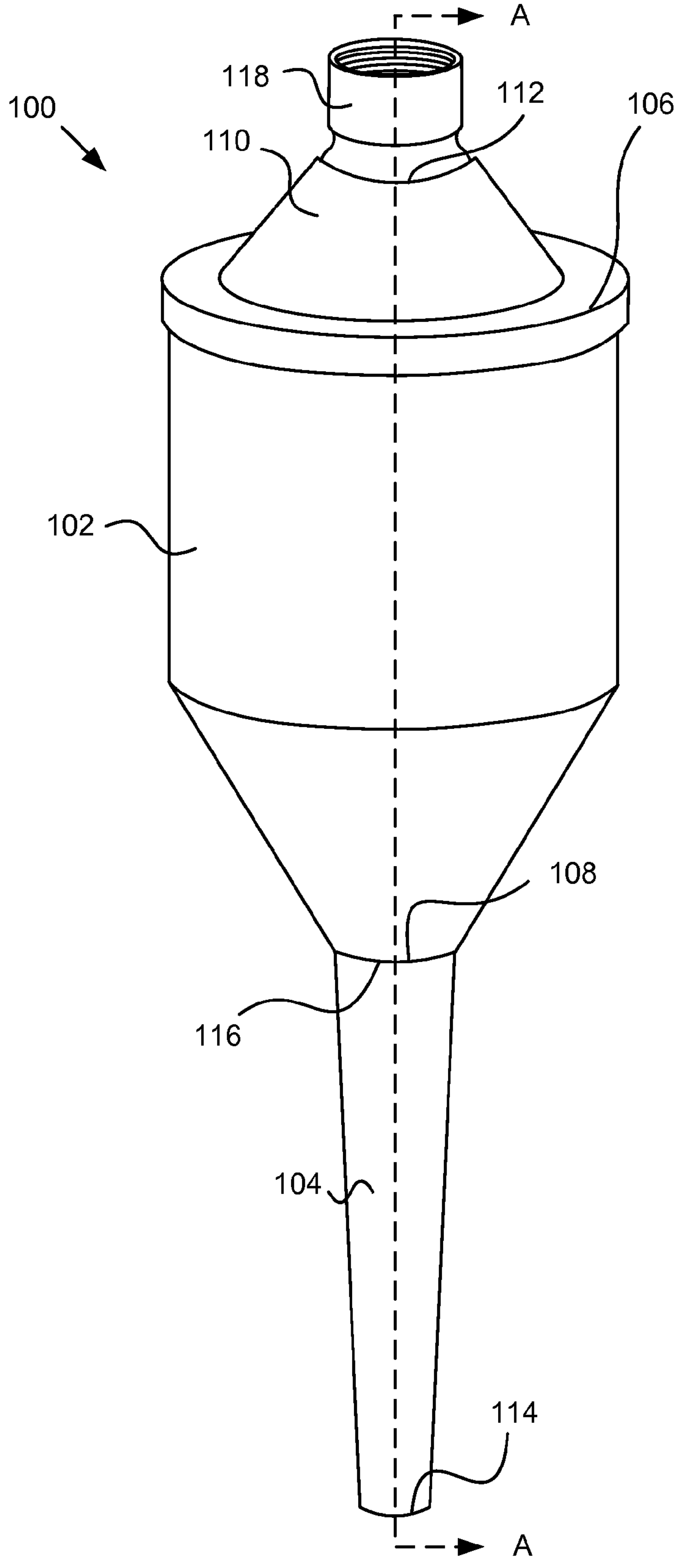
FIG. 1 depicts one embodiment of an apparatus for concentrating a stream of water.

FIG. 1 depicts one embodiment of an apparatus 100 for concentrating a stream of water. The apparatus 100, in certain embodiments, includes a chamber 102, a plurality of baffling elements 202 (FIG. 2), and a concentration member 104.

The chamber 102, in one embodiment, has a first end 106 and a second end 108. The first end 106 of the chamber 102 is disposed opposite the second end 108 of the chamber 102. The first end 106 of the chamber 102 is communicable in water receiving communication with a water source. For example, in one embodiment, the first end 106 of the chamber 102 is coupled to a conventional showerhead 110. In other embodiments, as further described below, the first end 106 of the chamber 102 may be directly coupled to a water source such as a shower outlet, a bathtub faucet, a hose, or other plumbing.

In certain embodiments, the first end 106 of the chamber 102 is attached to a coupling member 118. The coupling member 118 is removably coupleable to a shower outlet such as the plumbing extending from a shower wall. In the embodiment depicted in FIG. 1, the coupling member 118 is a threaded portion of a conventional showerhead 110. In other embodiments, as discussed below, the coupling member 118 may be a threaded portion integrally coupled to the chamber 102 (See, FIG. 6). In certain embodiments, such as embodiments wherein the coupling member is a threaded portion integrally coupled to the chamber 102, because the coupling member 118 is removably coupleable to a shower outlet, the apparatus 100 can be easily interchanged with a conventional showerhead.

In embodiments wherein the chamber 102 is coupled to a conventional showerhead 110, the showerhead 110 may include a ball joint 112. Where the apparatus 100 is coupled to rigid plumbing such as rigid plumbing extending from a shower outlet, the ball joint 112 allows adjustment of a direction of a stream of water exiting the apparatus 100 from a water dispensing end 114 of the concentration member 104. In certain embodiments, the ball joint 112 facilitates adjusting the direction of the stream of water in an infinite number of directions.

As further discussed below, the apparatus 100 receives water from a water source such as conventional household plumbing at the first end 106 of the chamber 102. The water travels through the chamber 102 and is delivered to a water receiving end 116 of the concentration member 104 through the second end 108 of the chamber 102. Thus, in certain embodiments, the water receiving end 116 of the concentration member 104 is communicable in water receiving communication with the second end 108 of the chamber 102. The water received from the second end 108 of the chamber 102 travels through the concentration member 104 and exits the concentration member 104 from the water dispensing end 114.

The apparatus 100, in one embodiment, may be used as a personal massaging device that uses hydro massage therapy to relieve muscle pain and/or stimulate a user. Hydro massage is a type of massage based on therapeutic use of water. Hydro massage therapy can help alleviate muscle and soft tissue injuries by applying a concentrated flow of water to a targeted area on a user's body. Hydro massage can also be used as a personal sexual gratification technique. For example, in certain embodiments, a user may direct the flow of water exiting the water dispensing end 114 of the concentration member 104 to the user's genitalia or other erogenous zone. The apparatus 100 concentrates the flow of water to provide a flow of water having an increased water pressure than would otherwise be available using a conventional showerhead or bathtub faucet. Additionally, in one embodiment, the apparatus 100 may be configured to provide a pulsating flow of water to the user's genitalia. The concentrated and/or pulsating flow of water stimulates the user's genitalia. In certain embodiments, the stimulation of the user's genitalia may provide an orgasmic response in the user.

Figure 2:
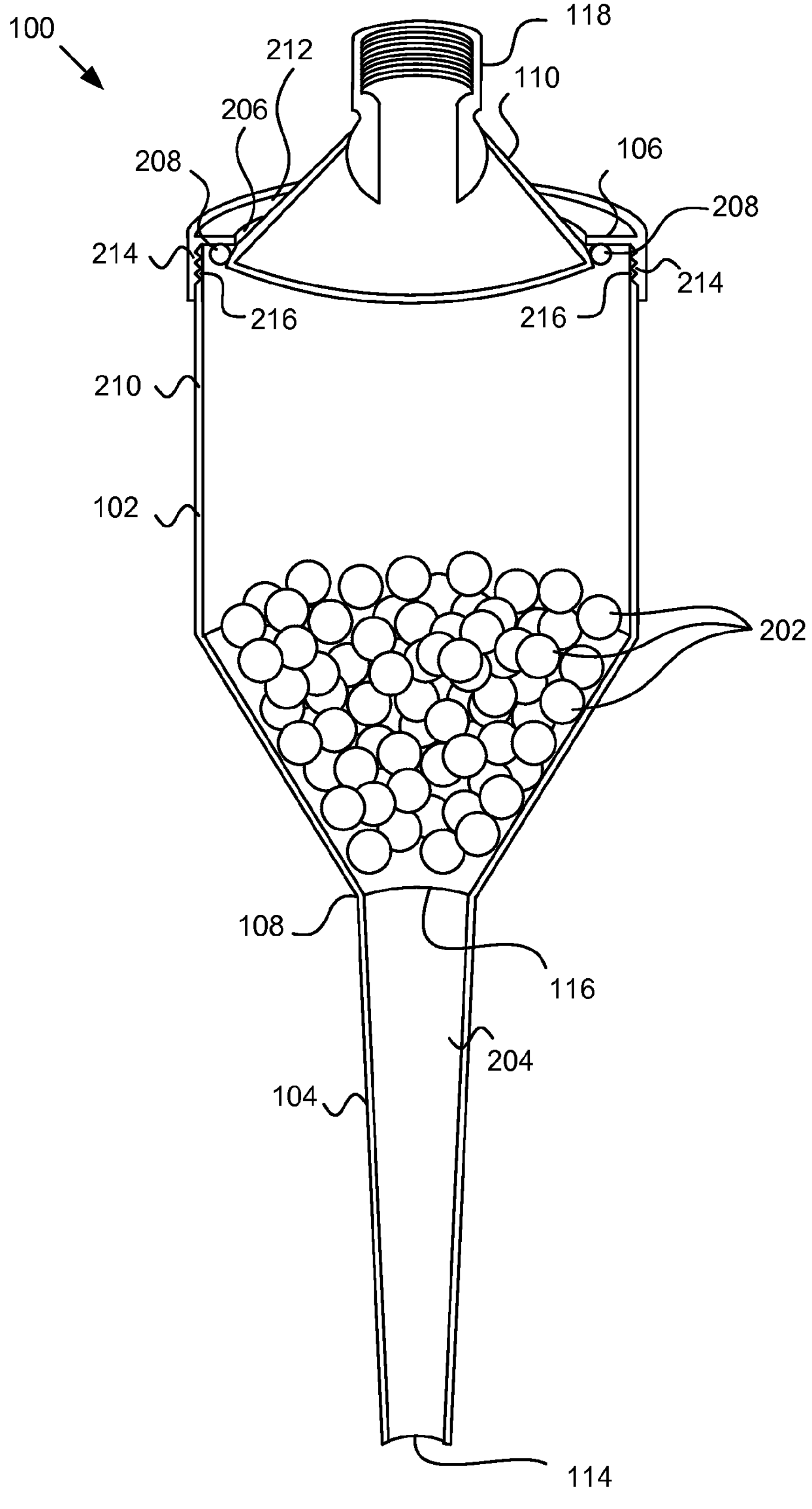
FIG. 2 depicts one embodiment of a cutaway view taken along line A-A of FIG. 1 of the apparatus for concentrating a stream of water.

FIG. 2 depicts one embodiment of a cutaway view of an apparatus 100 for concentrating a stream of water. The cutaway view depicted in FIG. 2 is taken along line A-A of FIG. 1. As illustrated, the concentration member 104 defines a channel 204. The channel 204 has a converging cross-sectional areal in a direction from the water receiving end 116 to the water dispensing end 114 such that the channel 204 is tapered to concentrate the water exiting the water dispensing end 114 of the concentration member 104. In other words, in one embodiment, the inner diameter of the channel 204 at the water receiving end 116 is substantially larger than the inner diameter of the channel 204 at the water dispensing end 114.

One of skill in the art will recognize that the decreased diameter of the channel 204 from the water receiving end 116 to the water dispensing end creates a Venturi effect. A Venturi effect is a jet effect wherein the velocity of a fluid increases as a cross-sectional area decreases. According to the laws governing fluid dynamics, a fluid's velocity increases as it passes through a constriction to satisfy the conservation of mass law which states that the mass of a closed system will remain constant over time. That is, mass cannot be created or destroyed. Thus, as water flows from the water receiving end 116 of the concentration member 104 to the water dispensing end 114, the velocity of the water increases. As a result, water exiting the water dispensing end 116 of the concentration member 104 exits with an increased velocity relative to the velocity of the water that enters the water receiving end 114 of the concentration member 104. The stream of water exiting the water dispensing end 116, having an increased velocity, can be directed to an area on the user's body for therapeutical purposes such as to massage the area. In certain embodiments, the stream of water exiting the water dispensing end 116 may directed at a user's genitals to massage the user's genitals and induce an orgasm in the user.

In one embodiment, the chamber 102 includes two independent components, a body portion 210 and a capping portion 212. In such an embodiment, the capping portion 212 of the chamber 104 includes an aperture 206 through which the showerhead 110 is received. The aperture 206 has an inner diameter substantially smaller than an outer diameter of the showerhead 110 at the widest point of the showerhead 110. A sealing member 208 is positioned around the showerhead 110 to seal the aperture 206. The sealing member 208 creates a watertight seal between the showerhead and the capping member 212 to maintain water within the chamber 102.

In one embodiment, the capping member 212 includes threads 214 which are matingly receivable on threads 216 disposed on the body portion 210 of the chamber 102. Thus, in one embodiment, the capping member 212 is removable from the body portion 210 to facilitate insertion of the showerhead 110 into the aperture 206. Once the showerhead 110 is positioned within the aperture 206, the capping member 212 is coupled to the body portion 210 to seal the chamber 102. With the showerhead 110 coupled to the chamber 102, the showerhead 110 can be attached to a shower outlet extending from a shower wall using the threaded coupling member 118 of the showerhead 110 as is known in the art.

As discussed above, in certain embodiments, a plurality of baffling elements 202 may be positioned within the chamber 102 of the apparatus 100. The plurality of baffling elements 202 operate to interrupt or restrain the flow of water from the first end 106 of the chamber 102 to the second end 108 of the chamber 102. In the embodiment illustrated in FIG. 2, the plurality of baffling elements 202 are depicted as spherical elements. One of skill in the art will recognize that in other embodiments, the baffling elements 202 may be any other geometric shape.

By positioning a plurality of baffling elements within the path of a stream of water traveling through the chamber 102, the present subject matter takes advantage of Bernoulli's principal to create turbulence in the stream of water. The turbulence causes the flow of the stream of water to oscillate which provides a massaging characteristic to the stream of water exiting the water dispensing end 116 of the concentration member 104.

Figure 3:
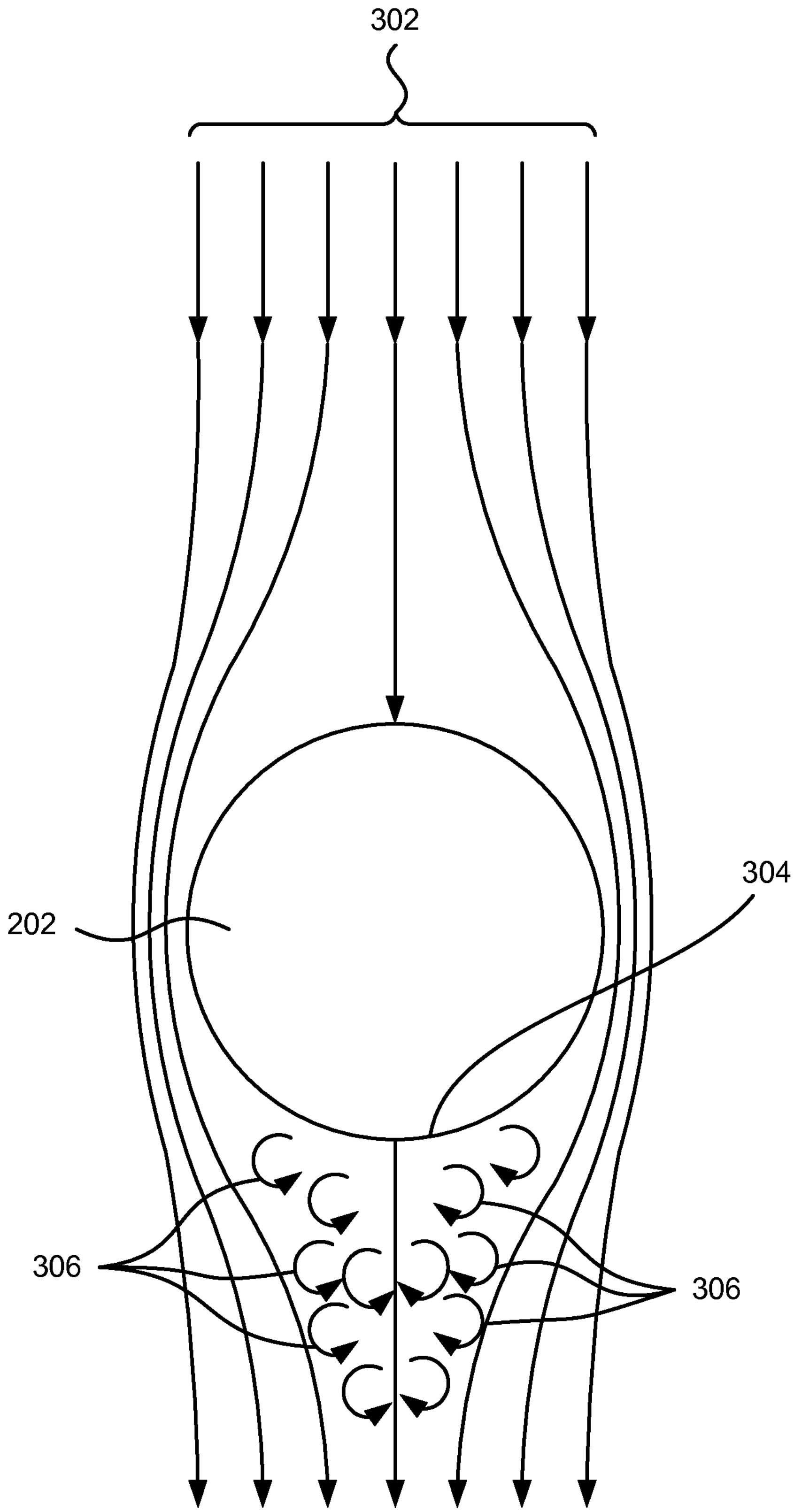
FIG. 3 depicts one embodiment of a baffling element positioned within a path of a stream of water.

FIG. 3 depicts one embodiment of a baffling element 202 positioned within a path of a stream of water 302. As water travels past one of the baffling elements 202, the movement of the water past the baffling element 202 creates a space devoid of downstream flowing water on the downstream side 304 of the baffling element 202. Water on the downstream side 304 of the baffling element 202 flows into the void creating a swirl of water on each edge of the baffling element 202 and a reverse flow of water, flowing back upstream towards the downstream side 304 of the baffling element 202 behind the baffling element as indicated by arrows 306. The turbulence and upstream flows caused by the baffling elements 202 cause an oscillation in the flow of water exiting the concentration member 104. The oscillation in the flow of water exiting the concentration member 104 creates a pleasant massaging flow that can be applied to a particular part of a user's body such as a sore muscle or the user's genitalia.

Figure 4:
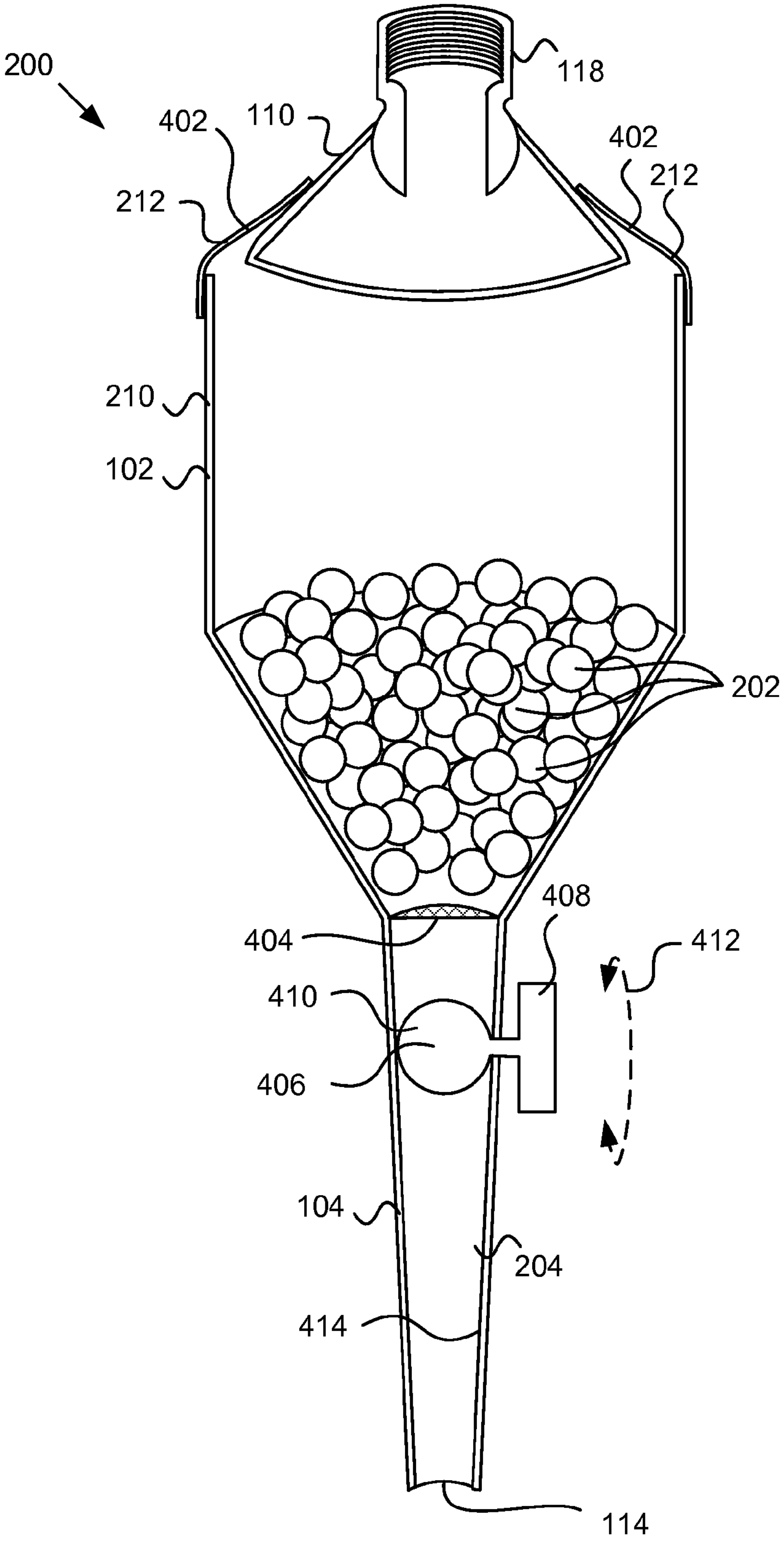
FIG. 4 depicts another cutaway view of one embodiment of an apparatus for concentrating a stream of water.

FIG. 4 depicts a cutaway view of another embodiment of an apparatus 200 for concentrating a stream of water. In certain embodiments, the apparatus 200 includes a chamber 102, a plurality of baffling elements 202, and a concentration member 104. In one embodiment, the plurality of baffling elements 202 are substantially similar to the baffling elements 202 discussed above with reference to FIG. 2.

The chamber 102, in one embodiment, includes as body portion 210 and a capping member 212. In certain embodiments, the body portion 210 is substantially similar to the body portion 210 discussed above with reference to FIG. 2. The capping member 212, in one embodiment, is a pliable membrane 402 that encircles the body portion 210 of the chamber 102 and the showerhead 110. The pliable membrane 402 is watertight and makes a seal with the body portion 210 of the chamber 102 and with the showerhead 110 such that water does not escape from within the chamber when the apparatus 200 is in use.

In certain embodiments, a filtering member 404 is positioned between the plurality of baffling elements 202 and the concentration member 104. The filtering member 404, in certain embodiments, keeps the plurality of baffling elements 202 positioned within the chamber 102. In one embodiment, the filtering member 404 is made of a screen material configured to allow water to flow into the concentration member 104 while keeping the plurality of baffling elements 202 positioned within the chamber 102. In another embodiment, as discussed in relation to FIG. 5A, the filtering member 404 is made from a substantially solid material 502 having at least one aperture 504 disposed through the substantially solid material 502.

In certain embodiments, the apparatus 200 includes a water velocity adjustment member 406 that adjusts a velocity of the water dispensed from the dispensing end 114 of the concentration member 104. The water velocity adjustment member 406 includes a manipulation flange 408 and a water blocking flange 410. To adjust the velocity of the water dispensed from the dispensing end 114 of the concentration member 404, a user rotates the manipulation flange 408 in the direction indicated by arrows 412. Rotating the manipulation flange 408 causes the water blocking flange 410 to rotate within the channel 204 defined by the concentration member 104. As the water blocking flange 410 is rotated, the water blocking flange 410 blocks off more and more of the water traveling through the channel 204 restricting the flow of water through the channel 204. In certain embodiments, the water blocking flange 410 is shaped substantially similar to the inner surface 414 of the channel 204 such that upon sufficient rotation of the water blocking flange 410 the entire channel 204 is blocked. In such a position, no water passes the water blocking flange 410 such that the apparatus 200 is effectively turned off.

Figure 5A:
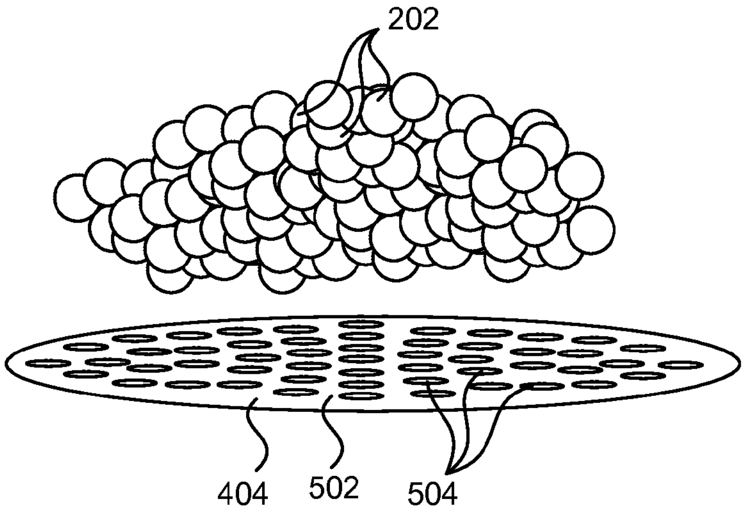
FIG. 5A depicts a side view of one embodiment of a filtering member positionable between a plurality of baffling members and a concentration member.

FIG. 5A depicts a side view of one embodiment of a filtering member 404. As discussed above, in certain embodiments, the filtering member 404 is made from a substantially solid material 502 having at least one aperture 504 disposed through the substantially solid material 502. In such an embodiment, the size of the at least one aperture 504 is substantially smaller than the size of each of the plurality of baffling elements 202 such that the plurality of baffling elements 202 are maintained within the chamber 102. Water, travels through the at least one aperture 504 and into the concentration member 104 where it is concentrated and its velocity is increased before exiting the water dispensing end 114 of the concentration member 104 as discussed above.

Figure 5B:
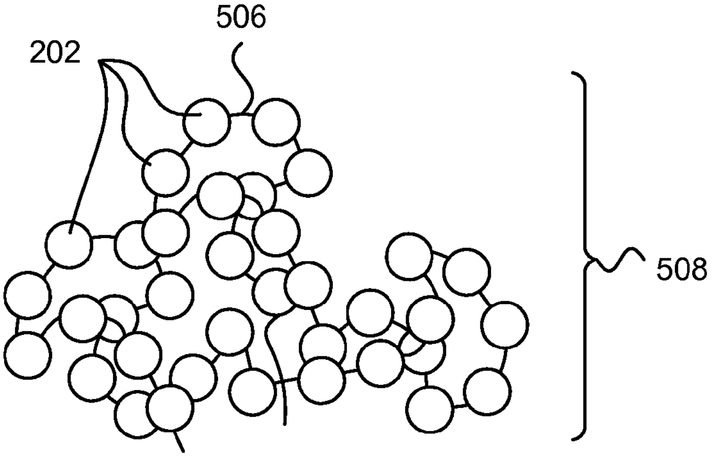
FIG. 5B depicts a side view of one embodiment of a plurality of baffling elements coupled to one another by a fiber to form a unified conglomerate of baffling elements.

FIG. 5B depicts a side view of one embodiment of a plurality of baffling elements 202. In certain embodiments, such as where a filtering member 404 is disposed between the plurality of baffling elements 202 and the concentration member 104, each baffling element 202 may be independent of one another. In other embodiments, such as the embodiment illustrated in FIG. 5B, an elongated fiber 506 may connect the baffling elements 202 to one another. Each baffling element 202 is attached to the elongated fiber 506 such that the baffling elements 202 form a unified conglomerate of baffling elements 508. While a single baffling element 202 may have a small enough diameter to fit within the concentration member 104, the unified conglomerate of baffling elements 508 have a large enough mass that the unified conglomerate of baffling elements 508 remains positioned within the chamber 102.

Figure 6:
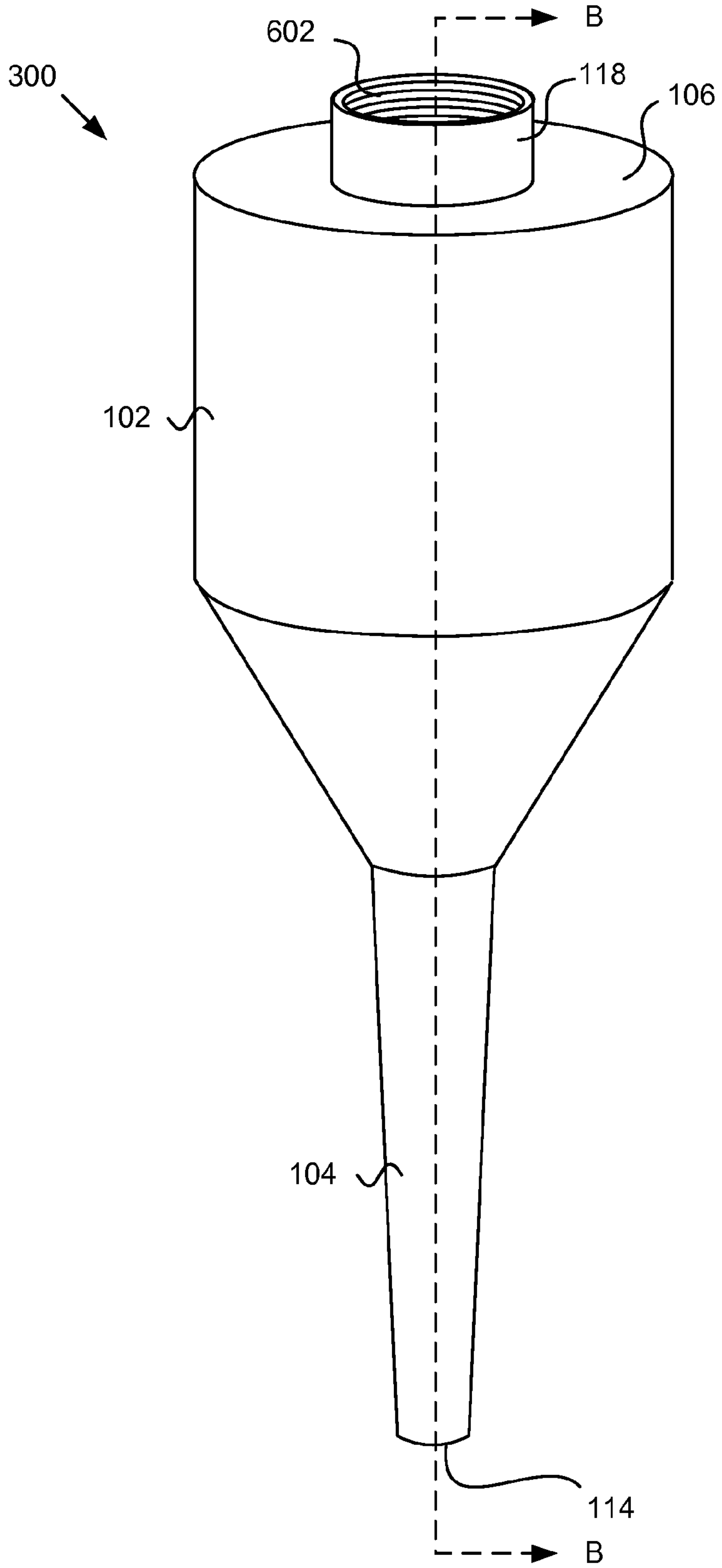
FIG. 6 depicts a side view of one embodiment of an apparatus for concentrating a stream of water.

FIG. 6 depicts a side view of one embodiment of an apparatus 300 for concentrating a stream of water. In certain embodiments, the apparatus 300 includes a chamber 102, a plurality of baffling elements 202, and a concentration member 104. In one embodiment, the plurality of baffling elements 202 and the concentration member 104 are substantially similar to the plurality of baffling elements 202 and the concentration member 104 discussed above.

The chamber 102, in certain embodiments, may be a single integral unit having a coupling element 118 attached to a first end 106 of the chamber 102. Thus, in certain embodiments, instead of coupling the chamber 102 to a conventional showerhead 110, the coupling element 118 may be integral with the first end 106 of the chamber 102 and may couple directly to a shower outlet on a shower wall. In such an embodiment, the coupling between the coupling element 118 and the first end 106 of the chamber 102 may include a ball joint (not shown), such as the ball joint 112 discussed above. A ball joint coupling between the coupling element 118 and the first end 106 of the chamber 102 may facilitate aiming of the stream of water dispensed from the dispensing end 114 of the concentration member 104.

In certain embodiments, the coupling member 118 includes a plurality of threads 602 sized and shaped to matingly receive threads on a shower outlet from a shower wall. Thus, in one embodiment, the apparatus 300 is easily interchangeable with a conventional showerhead such as showerhead 110 discussed above. When a user desires a massage or desires sexual gratification from the apparatus 300, the user may simply remove the conventional showerhead 110 and replace it with the apparatus 300. Once the user has completed their massage or has achieved sexual gratification, the conventional showerhead 110 may be replaced for future showering.

Figure 7:
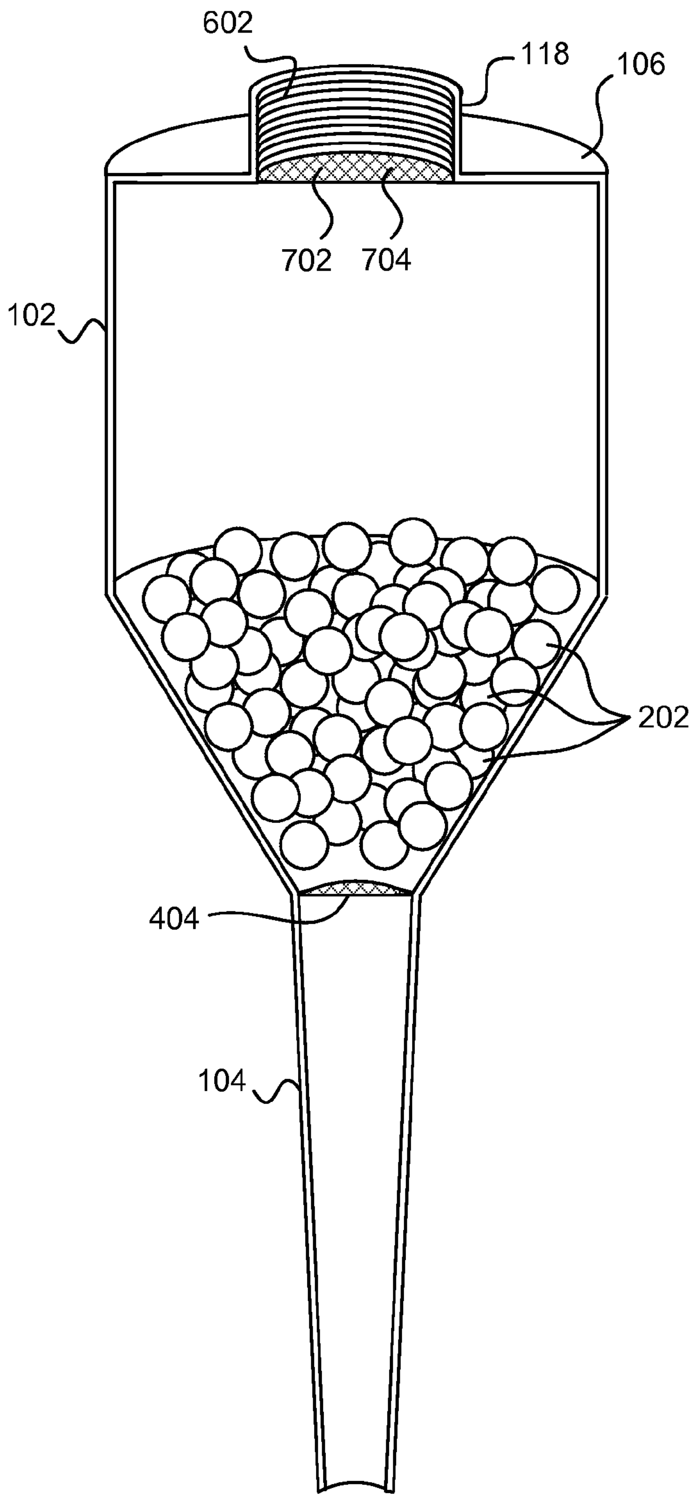
FIG. 7 depicts one embodiment of a cutaway view taken along line B-B of FIG. 6 of the apparatus for concentrating a stream of water.

FIG. 7 depicts one embodiment of a cutaway view of an apparatus 300 for concentrating a stream of water. The cutaway view depicted in FIG. 7 is taken along line B-B of FIG. 6. The embodiment depicted in FIG. 7 illustrates the integral nature between the coupling member 118 and the first end 106 of the chamber 102. In one embodiment, the chamber 102 and the coupling member 118 may be integrally molded in a single mold. In other embodiments, the coupling member 118 and the chamber 102 may be molded separately and coupled to one another by a chemical adhesive.

In certain embodiments, the center portion 704 of the coupling member is open to the chamber 102 such that the first end 106 of the chamber is communicable in water receiving communication with a water source such as a shower outlet. In such an embodiment, a screening element 702 may be positioned within the center portion 704 of the coupling member to maintain the plurality of baffling elements 202 within the chamber 102. In such an embodiment, the filtering member 404 may also be positioned between the plurality of baffling elements 202 and the concentration member 104 to make sure the plurality of baffling elements does not enter into or fall out of the concentration member 102. Of course, one of skill in the art will recognize that in embodiments where the plurality of baffling elements 202 are coupled to one another by a fiber 506 to form a unified conglomerate of baffling elements 508, the unified conglomerate of baffling elements 508 may be sufficiently large to keep the unified conglomerate of baffling elements 508 positioned within the chamber 102.

Figure 8:
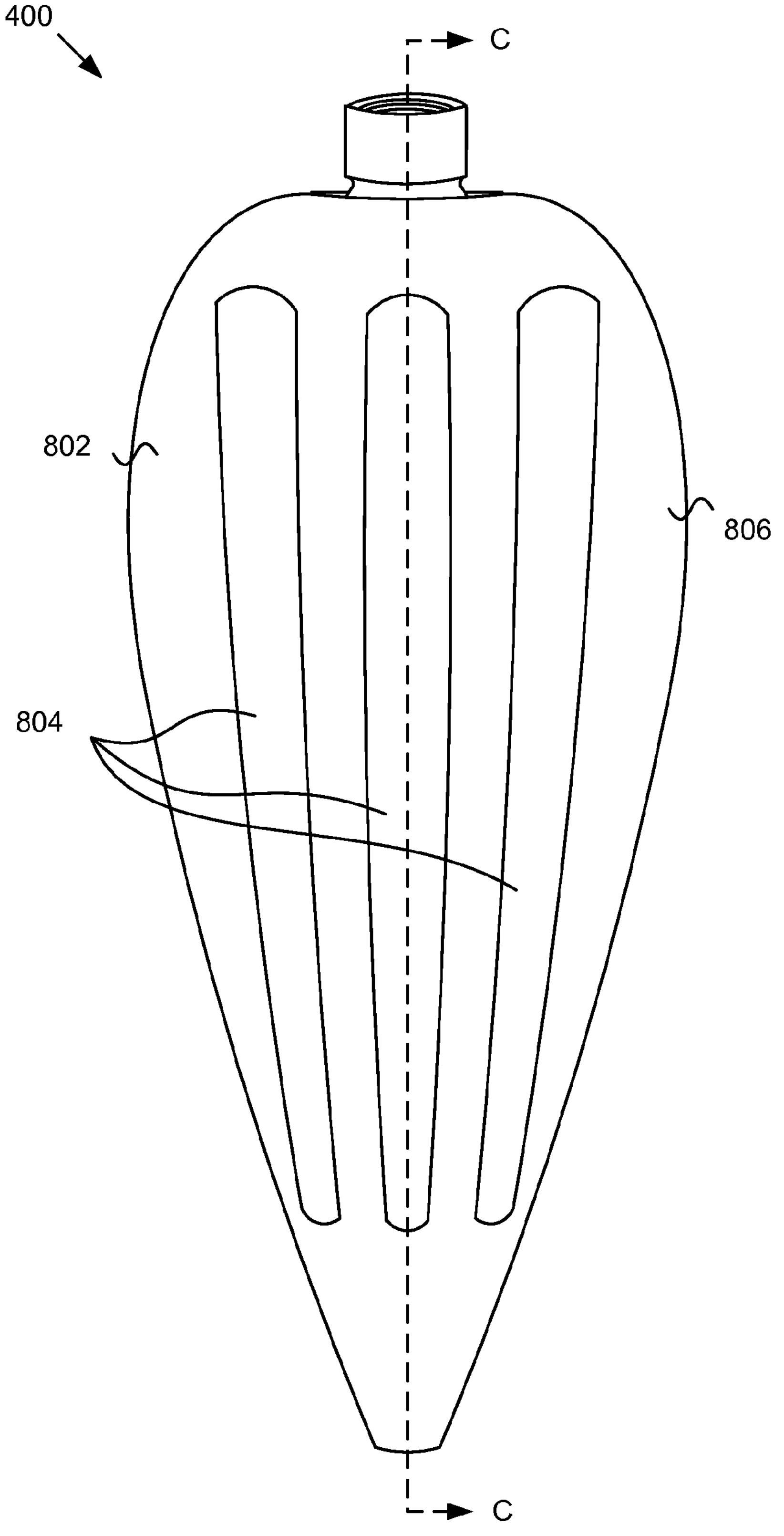
FIG. 8 depicts a side view of one embodiment of an apparatus for concentrating a stream of water.

FIG. 8 depicts a side view of one embodiment of an apparatus 400 for concentrating a stream of water. In certain embodiments, the apparatus 400 includes a decorative covering 802 that covers a coupling member 902 (FIG. 9), a chamber 904 (FIG. 9), and a concentration member 906 (FIG. 9).

The decorative covering 802, in one embodiment, is simply a covering that shields the coupling member, the chamber 904, and the concentration member 906 from view. In other embodiments, the decorative covering 802 may include one or more gripping elements 804 disposed in or one an outer surface 806 of the decorative covering 802. In such an embodiment, the gripping elements 804 on the outer surface 806 of the decorative covering 802 may be used to assist a user in aiming the apparatus 400.

Figure 9:
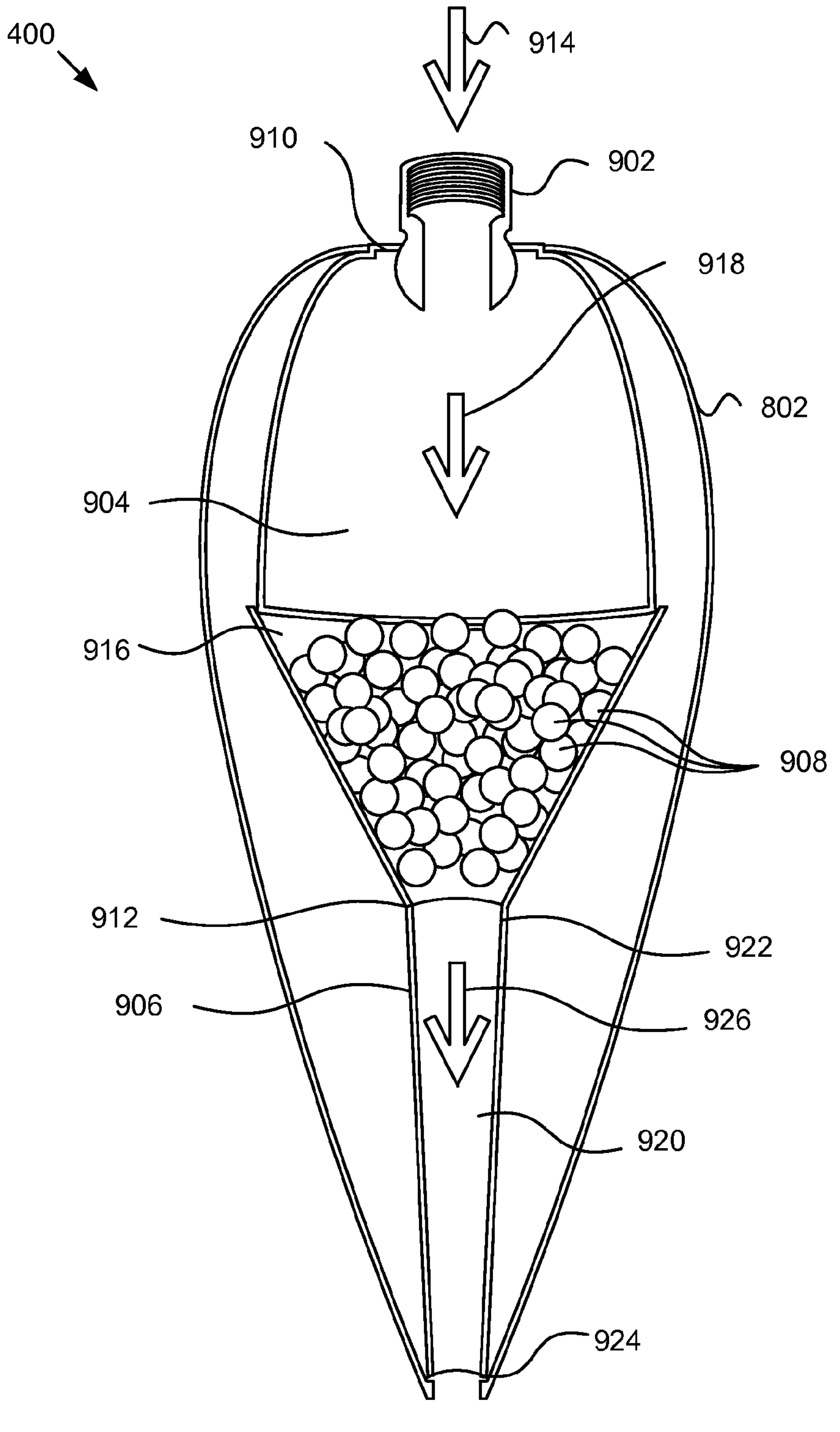
FIG. 9 depicts one embodiment of a cutaway view taken along line C-C of FIG. 8 of the apparatus for concentrating a stream of water.

FIG. 9 depicts one embodiment of a cutaway view of an apparatus 400 for concentrating a stream of water. The cutaway view depicted in FIG. 7 is taken along line C-C of FIG. 8. In certain embodiments, the apparatus 400 includes a decorative covering 802, a coupling member 902, a chamber 904, and a concentration member 906. In one embodiment, the apparatus 400 also includes a plurality of baffling elements 908. While the embodiments illustrated in FIGS. 8 and 9 discuss the elements of the apparatus using a different series of numerals, one of skill in the art will recognize that in certain embodiments the coupling member 902, the chamber 904, the concentration member 906, and the baffling elements 908 may be substantially similar to the coupling member 118, the chamber 102, the concentration member 104, and the baffling elements 908 discussed above.

In one embodiment, the coupling member 902 and the chamber 904 may be a conventional showerhead. In other embodiments, the coupling member 902 and the chamber 904 may be discrete elements with the coupling member 902 configured to couple the apparatus 400 to a water source (i.e., household plumbing) and the chamber 904 configured to collect water and to retain the plurality of baffling elements 908.

The chamber 904 includes a first end 910 and a second end 912 with the first end 910 communicable in water receiving communication with the water source such that water from the water source enters the apparatus 400 in the direction indicated by arrow 914. In certain embodiments, such as where the coupling member 902 and the chamber 904 are a conventional showerhead, a top portion 916 of the concentration member 906 may define a portion of the chamber 904. In such an embodiment, the concentration member 906 may be formed from a conventional funnel.

Water is received within the chamber 904 and travels through the chamber in the direction indicated by arrow 918 until the water encounters a plurality of baffling elements 908 positioned within the chamber 904. In certain embodiments, the baffling elements 908 interrupt a flow of water traveling from the first end 910 of the chamber 904 to the second end 912 of the chamber 904. This interruption imparts a vibratory effect to the flow of water flowing past the baffling elements 908.

In one embodiment, the vibratory effect may be altered or changed by selecting a different size, shape or number of baffling elements 908. For example, in certain embodiments, the baffling elements 908 may be substantially spherical elements (i.e., beads). In an exemplary embodiment, the diameter of an outermost surface of each baffling element 908 may be between about 3/16 and 1/2 of an inch. Baffling elements 908 having these dimensions have been found to produce a soothing and enjoyable vibratory effect.

In one embodiment, the apparatus 400 may include about 85 baffling elements 908 with each baffling element 908 coupled to at least one other baffling element 908 by an elongated fiber. As discussed above, in certain embodiments, the elongated fiber retains the baffling elements 908 in a substantially conglomerated bulk of baffling elements 908. In such an embodiment, the size conglomerated bulk of baffling elements 908 may be sufficient to keep the baffling elements from entering the concentration member 906. In other embodiments, a filtering member 404 (FIG. 4) may be positioned between the plurality of baffling elements 908 and the concentration member 906 to keep the baffling elements 908 positioned within the chamber 904.

The concentration member 906 defines a channel 920 that extends from a water receiving end 922 to a water dispensing end 924. The water receiving end 922 of the channel 920 is communicable in water receiving communication with water flowing past the baffling elements 908. The channel 920 has a converging cross-sectional area in a direction from the water receiving end 922 to the water dispensing end 924. That is, a diameter of the channel 920 at the water receiving end 922 is substantially larger than a diameter of the channel 920 at the water dispensing end 924 such that water traveling through the channel 920 in the direction indicated by arrow 926 is condensed and compressed to increase the water pressure as it exits the dispensing end 924 of the channel 920.

In an exemplary embodiment, it has been found that a concentration member 906 with a channel 920 having an inner diameter at the water receiving end 922 of between about 3/4 and 1 1/4 of an inch produces a pleasurable amount of pressure where the inner diameter of the water dispensing end 924 of the channel 920 is between about 1/16 and 7/16 of an inch. Of course, one of skill in the art will recognize that the inner diameter of the channel 920 at the water receiving end 922 and the inner diameter of the water dispensing end 924 of the channel 920 may be altered while retaining approximately the same ratio of diameter sizes to achieve the same pleasurable amount of pressure.

The apparatus 400, in an exemplary embodiment, uses a conventional shower head coupled to a funneling apparatus and sealed at the coupling between the showerhead and funneling apparatus to create a chamber 904. Baffling elements 908 interrupt the flow of water to transform the water into a more solid tube-like structure. The water is compressed as it flows through the concentration member 906. The water exits the apparatus 400 in a solid flow.

In certain embodiments, a diameter of the tube-like flow of water may be altered depending on whether a male or female will be using the apparatus 400. In other embodiments, the diameter of the tube-like flow of water may be altered based on a user's personal preferences rather than a sex of the user. In one embodiment, a screen may be positioned within the path of the water to act as an aerator to change the intensity of the pressure and vibration (i.e., to lessen the pressure and/or intensity). Such an apparatus may be particularly attractive to female users who may wish to have lighter pressure or intensity.

In certain embodiments, the diameter of the tube-like flow of water may be altered by changing the inner diameter of the water dispensing end 924 of the channel 920. The intensity or pressure of the water exiting the inner diameter of the of the channel 920 may be altered by changing the ratio of the inner diameter of the water receiving end 922 to the inner diameter of the water dispensing end 924.

In one embodiment, the apparatus 400 is hands free. That is, the stream of water just needs to be pointed at the appropriate place and the apparatus 400 does the work. As the water exits the apparatus 400 and flows downward, the water takes on a vibrating effect and pressure as it impacts the body. The farther the water falls, the stronger the pressure on impact. In case of a female user, the apparatus 400 has been found to be best used with the user positioned in a standing position. For males the apparatus 400 has been found to be best used with the user lying in a prone position at the bottom of a shower where the flow of water takes on a more powerful pressure from the longer fall of the water from the apparatus. In certain embodiments, both male and females enjoy the constant vibration and pressure that may invoke an orgasm. In one embodiment, the orgasm may be particularly intense.

Research indicates that the apparatus 400 may save up to 35% of the flow of water compared to a traditional 2.5 GPM shower head. Research also indicates that less hot water may be used when using the apparatus 400 due to the fact that heat in the solid flow of water is maintained better than with a traditional shower head where the heat is more readily lost as the water is diffused into smaller droplets.

In one embodiment, the apparatus 400 may be used in place of a traditional shower head. Because the decorative covering 802 is relatively ambiguous and fails to indicate anything of a sexual nature, the user need not worry about being embarrassed by having the device attached to a house hold water source. is In other embodiments, the apparatus 400 may be used when needed for its intended purpose, and then be replaced by a traditional shower head after usage, all depending on the user's individual preference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for manipulating a user's erogenous zone, the apparatus comprising:

a chamber having a first end opposing a second end, the first end of the chamber communicable in water receiving communication with a water source;

a plurality of baffling elements disposed within the chamber, the plurality of baffling elements configured to interrupt a flow of water received from the first end of the chamber;

a concentration member that defines a channel, the concentration member having a water receiving end and a water dispensing end, wherein the channel has a converging cross-sectional area in a direction from the water receiving end to the water dispensing end, the water receiving end communicable in water receiving communication with water flowing past the baffling elements; and an elongated fiber, wherein the plurality of baffling elements are coupled to the elongated fiber.

2. The apparatus of claim 1, further comprising a coupling member attached to the first end of the chamber, the coupling member removably coupleable with a shower outlet.

3. The apparatus of claim 2, wherein the coupling member is removably coupleable with a conventional shower head.

4. The apparatus of claim 1, wherein the plurality of baffling elements comprise a plurality of beads.

5. The apparatus of claim 4, wherein each bead in the plurality of beads is substantially spherical.

6. The apparatus of claim 5, wherein a diameter of an outermost surface of each bead in the plurality of beads is between about 3⁄16 and ½ of an inch.

7. The apparatus of claim 1, wherein at least one of a size, a shape, and a number of the baffling elements is selected to impart a vibratory effect to the flow of water flowing past the baffling elements.

8. The apparatus of claim 1, wherein the elongated fiber retains the plurality of baffling elements in a unified conglomerate of baffling elements.

9. The apparatus of claim 1, further comprising a filtering member positioned between the plurality of baffling members and the concentration member, the filtering member having at least one aperture, wherein a size of the at least one aperture is substantially smaller than a size of each of the plurality of baffling members.

10. The apparatus of claim 1, wherein an inner diameter of the water receiving end of the concentration member is between about ¾ and 1¼ of an inch and wherein an inner diameter of the water dispensing end is between about 1⁄16 and 7⁄16 of an inch.

11. The apparatus of claim 1, further comprising a water velocity adjustment member, the water velocity adjustment member configured to adjust a velocity of the water dispensed from the dispensing end of the concentration member.

12. An apparatus for concentrating a stream of water, the apparatus comprising:

a chamber having a first end opposing a second end, the first end of the chamber communicable in water receiving communication with a water source;

a plurality of substantially spherical beads disposed within the chamber, the plurality of substantially spherical beads positioned within a path of a flow of water from the first end of the chamber to the second end of the chamber to interrupt the flow of water;

a concentration member that defines a channel, the concentration member having a water receiving end and a water dispensing end, wherein the channel has a converging cross-sectional area in a direction from the water receiving end to the water dispensing end, the water receiving end communicable in water receiving communication with water flowing past the substantially spherical beads; and an elongated fiber, wherein the plurality of substantially spherical beads are coupled to the elongated fiber and wherein the elongated fiber retains the plurality of beads in a unified conglomerate of spherical beads.

13. The apparatus of claim 12, wherein at least one of a size and a number of the plurality of substantially spherical beads is selected to impart a vibratory effect to the flow of water flowing past the substantially spherical beads.

14. The apparatus of claim 12, wherein a diameter of an outermost surface of each bead in the plurality of beads is between about 3⁄16 and ½ of an inch.

15. The apparatus of claim 12, wherein an inner diameter of the water receiving end of the concentration member is between about ¾ and 1¼ of an inch and wherein an inner diameter of the water dispensing end is between about 1⁄16 and 7⁄16 of an inch.

16. A system for concentrating a stream of water, the system comprising:

a chamber having a first end opposing a second end;

a coupling member attached to the first end of the chamber, the coupling member removably coupleable with a shower outlet such that the first end of the chamber is communicable in water receiving communication with a water source;

a plurality of baffling elements disposed within the chamber, the plurality of baffling elements configured to interrupt a flow of water received from the first end of the chamber;

a concentration member that defines a channel, the concentration member having a water receiving end and a water dispensing end, wherein the channel has a converging cross-sectional area in a direction from the water receiving end to the water dispensing end, the water receiving end communicable in water receiving communication with water flowing past the baffling elements; and an elongated fiber, wherein the plurality of baffling elements are coupled to the elongated fiber.

17. The apparatus of claim 16, wherein the plurality of baffling elements comprise a plurality of substantially spherical beads arranged in a unified conglomerate of spherical beads.

18. The apparatus of claim 16, wherein at least one of a size, a shape, and a number of the baffling elements is selected to impart a vibratory effect to the flow of water flowing past the baffling elements.

* * * * *